United States Patent
Wong et al.

(10) Patent No.: US 10,052,430 B2
(45) Date of Patent: Aug. 21, 2018

(54) PRESSURE RELIEF VALVE FOR CARDIOPULMONARY BYPASS

(71) Applicant: AMT Pte Ltd, Singapore (SG)

(72) Inventors: Martin Kok Soon Wong, Singapore (SG); Pheng Meng Tan, Singapore (SG); Chikashige Kiyoshi, Singapore (SG)

(73) Assignee: AMT PTE. LTD., Singapore (SG)

( * ) Notice: Subject to any disclaimer, the term of this patent is extended or adjusted under 35 U.S.C. 154(b) by 511 days.

(21) Appl. No.: 14/879,819

(22) Filed: Oct. 9, 2015

(65) Prior Publication Data

US 2017/0100532 A1   Apr. 13, 2017

(51) Int. Cl.
*A61M 1/36* (2006.01)
*A61M 39/24* (2006.01)
*A61M 39/22* (2006.01)

(52) U.S. Cl.
CPC .......... *A61M 1/3666* (2013.01); *A61M 1/367* (2013.01); *A61M 39/24* (2013.01); *A61M 2039/226* (2013.01); *A61M 2039/242* (2013.01); *A61M 2039/2426* (2013.01); *A61M 2039/2433* (2013.01)

(58) Field of Classification Search
CPC .......... A61M 1/3666; A61M 2039/226; A61M 39/24; A61M 1/367; A61M 2039/242; A61M 2039/2426; A61M 2039/2433
See application file for complete search history.

(56) References Cited

U.S. PATENT DOCUMENTS

| | | | |
|---|---|---|---|
| 4,671,786 A | 6/1987 | Krug | |
| 4,758,224 A | 7/1988 | Siposs | |
| 5,707,356 A | 1/1998 | Paul | |
| 6,053,896 A | 4/2000 | Wilson et al. | |
| 6,960,180 B2 | 11/2005 | McIntosh | |

*Primary Examiner* — Leslie Deak
(74) *Attorney, Agent, or Firm* — Thomas Schneck

(57) ABSTRACT

A pressure relieve valve for cardio pulmonary bypass responsive to abnormal pressure changes due to kinks in conduits used with the valve. In this situation, a principal flow path through a duckbill valve can be bypassed by positive and negative secondary flow paths for pressure relief. The secondary flow paths exist using umbrella valves of opposite orientation blocking holes in a flange separating inlet and outlet extensions of a tubular central body housing the duckbill valve. Each umbrella valve is throttled with a nipple that moderates flow in each of the secondary flow paths for slowing pressure equalization.

11 Claims, 2 Drawing Sheets

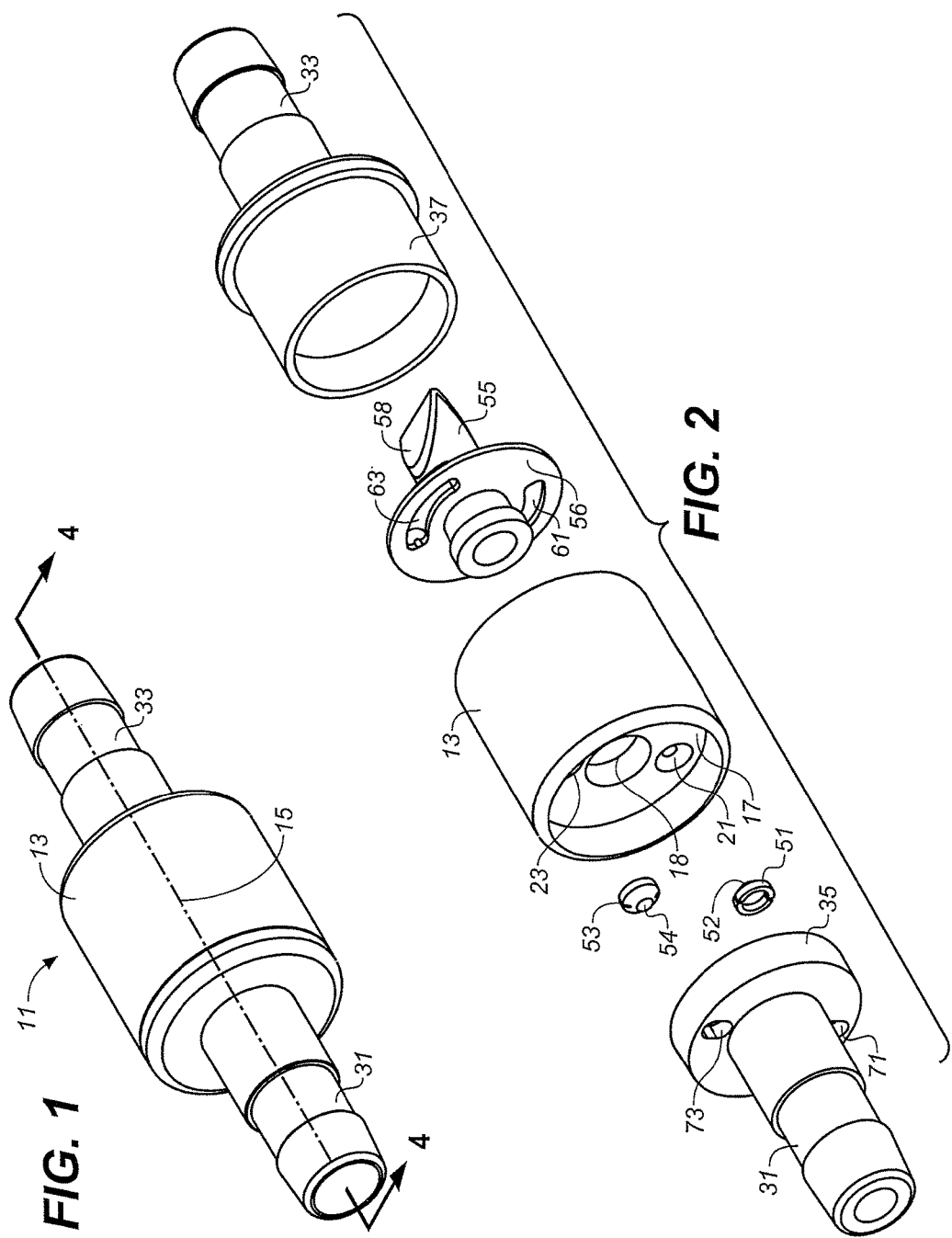

PRESSURE RELIEF VALVE FOR CARDIOPULMONARY BYPASS

TECHNICAL FIELD

The invention relates to valves used for pressure regulation in conduits inserted into the body during cardiac surgery and, more particularly, to a check valve responsive to abnormal pressure differences in such conduits.

BACKGROUND ART

In the book Cardiothoracic Surgery by J. Chikwe et al. (Oxford, $2^{nd}$ ed. 2013) there is a diagram of cardiopulmonary bypass (CPB) that provides a still, bloodless heart, while circulation to the rest of the body is maintained. In CPB, one of the safety components used in every system is a one-way valve in the left ventricular vent. Different designs for this one-way check valve are exemplified by the following prior art.

In U.S. Pat. No. 5,707,356 G. Paul discloses an overpressure check valve assembly for use during heart surgery. The assembly comprises an elongated tubular body portion having an inlet end, and an outlet end and a unidirectional valve disposed therebetween. A relief valve portion is joined to and in flow communication with the tubular portion. The relief valve portion includes a first relief valve configured to open if the pressure within the overpressure safety valve diminishes below a predetermined level, and a second relief valve configured to open if the pressure adjacent the outlet end exceeds a predetermined level. The first and second relief valves are disposed in a side by side configuration in a common conduit.

In U.S. Pat. No. 4,758,224 G. Siposs discloses a check valve that is positioned in the left ventricle drain line which permits flow only away from the heart. A vent valve is located downstream of the check valve to prevent buildup of pressure and includes an inwardly directed umbrella valve to limit left ventricle drain line vacuum intensity applied to the heart.

In U.S. Pat. No. 4,671,786 J. Krug discloses a safety check valve for heart surgery to prevent overpressure wherein the valve has an elongated tubular body portion with an inlet end, and an outlet end and a unidirectional valve disposed therebetween. A relief valve portion is joined to and in flow communication with the tubular portion. The relief valve portion includes a first relief valve configured to open if the pressure within the overpressure safety valve diminishes below a predetermined level, and a second relief valve configured to open if the pressure adjacent the outlet end exceeds a predetermined level.

While all of the prior art overpressure check valves are useful, a problem still exists in CPB where there is simultaneously some pressure from the heart or the pump circuit on the inlet side and some suction of blood or fluid by a pump on the outlet side. A pressure imbalance can occur due to kinks in conduits or improper connections of CPB lines on setup or line blockages. An object of the invention was to provide a CPB check valve that prevents one side from overpowering the other, particularly if a conduit kink, improper connection or line blockage should occur.

SUMMARY OF INVENTION

The above objective has been met with a CPB two-way valve that replaces one-way valves of the prior art. The new valve features a pair of nipples that throttle equalizing pressure fluid flow peripheral to a tubular duckbill one-way check valve. In other words, pressure imbalance through a duckbill valve caused by either the inlet or outlet being blocked prompts pressure equalizing flows through auxiliary positive and negative paths established through umbrella valves that control flow through holes in an annular flange that surrounds the duckbill valve. The positive and negative flow paths change the normal flow thorough the valve so that unsafe pressure, perhaps due to kinked conduits, can be relieved two-way. In the present invention, the pressure equalizing flow is throttled by nipples that have apertures that restrict flow through the hole, thereby improving safety of CPB valves by preventing sudden pressure changes.

BRIEF DESCRIPTION OF DRAWINGS

FIG. 1 is a front perspective view of a two-way valve for CPB.

FIG. 2 is a front perspective exploded view of the valve shown in FIG. 1.

DETAILED DESCRIPTION

Figure 3:
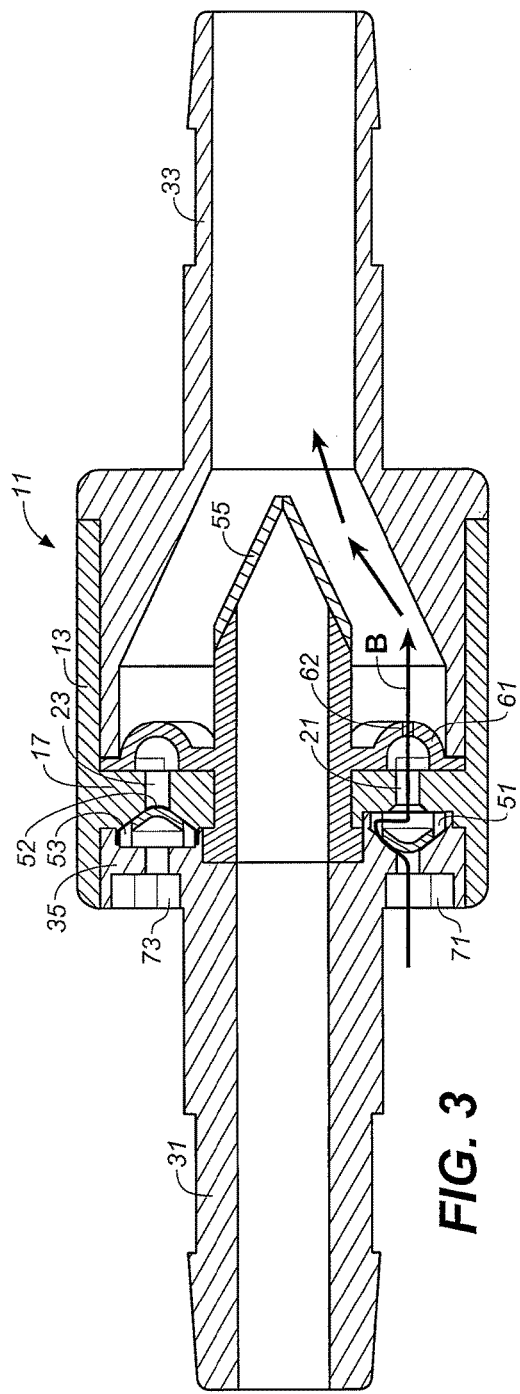
FIG. 3 is a first side cutaway operational view of the valve of FIG. 1.

With reference to FIG. 1, a valve 11 for CPB is shown having an axially symmetric appearance along longitudinal axis 15, indicated by a dashed line. The valve has a tubular outer body 13, a forward tubular inlet member 31, connected by tubing to the left ventricle, not shown. Ridges on the inlet member 31 frictionally engage the tubing. A rearward tubular outlet member 33 is connected by tubing to a pump. Similar ridges on the outlet member 33 engage the tubing. The forward inlet member 31 and rearward outlet member 33 are supported within the tubular outer body 13 by respective ends that are seated in the body.

With reference to FIG. 2, the forward inlet member 31 has an inner end 35, having a diameter that fits snugly in outer body 13. The inner end has a rim that allows the inner end 35 to abut the annular flange 17 that is part of outer body 13. The rearward outlet member 33 has an annular rim 37 that almost abuts annular flange 17 from the opposite side but sandwiches the duckbill valve 55 and its associated mounting disk 56. The duckbill valve 55 is made of al elastomer, preferably silicone rubber, with the forward flaps 58 biased by the rubber to be normally closed. Fluid pressure pushes the flaps open. On the opposite side of annular flange 17, the inner end 35 of inlet member 31 sandwiches umbrella valves 51 and 53 in place. The first umbrella valve 51 has an apex 52 facing a first hole 21 in flange 17. The second umbrella valve 53 has an apex 54 facing away from the second hole 23. The principal flow path through outer body 13 is through inlet member 31, axial hole 18 in outer body 13, through duckbill valve 55 and into the outlet member 33.

The duckbill mounting disk 56 has first and second nipples 61 and 63 in convex relation relative to holes 21 and 23 in outer body 13. The nipples are supported by disk 56, transverse to the axis of body 13. The nipples, having small control apertures, face in the same axial direction. Secondary flow paths on opposite sides of the duckbill valve exist. A positive pressure secondary flow path is through a hole 73 in the inner end 35 of inlet member 31, then through second umbrella valve 53, hole 23 and second nipple 63. A negative pressure secondary flow path is through hole 71 in the inner end 35 of inlet member 31, then through first umbrella valve 51, hole 21 and first nipple 61. The positive and negative secondary flow paths are safety flow paths for the situation when abnormal pressure imbalance exists on opposite sides of the duckbill valve, as when one of the inlets or outlets is blocked.

FIG. 3 illustrates the situation when the inlet member 31 is blocked or inlet tubing, not shown, is kinked. The duckbill valve 55 will close and the outlet member 33 will experience lower pressure, termed negative pressure, than when the duckbill valve is open accommodating flow through inlet member 31. In this situation, ambient pressure is higher outside of the valve 11 than inside and the secondary negative pressure flow path is activated. Low pressure in outlet member 33 pulls ambient air through hole 71, around the peripheral edges of first umbrella valve 51, through hole 21 and into first nipple 61 where the flow is throttled by a nipple aperture 62 that has a size determined by calibration to provide a desired flow rate considering other equipment in the CPB arrangement. The flow path is indicated by the arrow B. The higher outside pressure keeps the second umbrella valve 53 in place with pressure sensed through hole 73 in the inner end 35 of inlet member 31. Fluid flow through hole 23 in annular flange 17 is blocked. Flow in the secondary negative pressure flow path continues until the inlet is no longer blocked and the duckbill valve is open.

Figure 4:
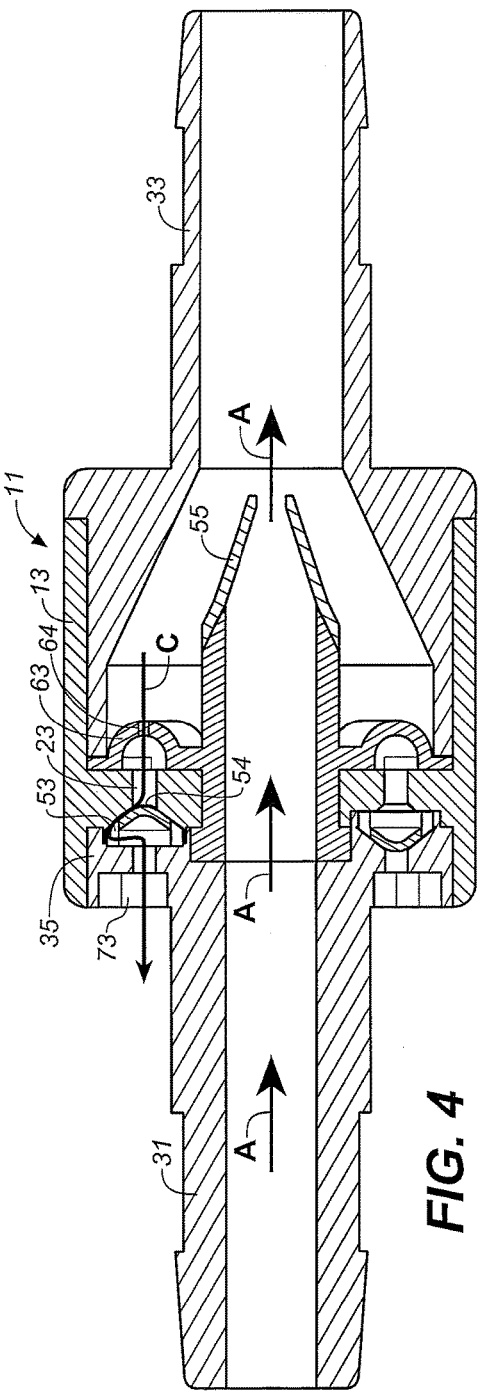
FIG. 4 is a second side cutaway operational view of the valve of FIG. 1.

FIG. 4 illustrates the situation where the outlet member 33 is blocked or outlet tubing is kinked. Duckbill valve 55 is open to fluid flow indicated by arrows A. If a fluid cannot freely exit outlet member 33, a higher pressure, termed positive pressure, exists without the outlet member than when free flow exists. In this situation a pressure equalizing flow is established in the secondary positive flow path. This flow, indicated by arrow C, is into second nipple 63 via central nipple aperture 64, then into hole 23 in outer body 13, pushing against the apex 54 of second umbrella valve 53 and then through hole 73 in the inner end 35 of inlet member 31. The duckbill valve 55 is a one way check valve.

In the present invention, the one way duckbill valve 55 is housed coaxially within a two way, positive and negative flow, valve structure, operating as the primary flow path through the valve at a regular, established pressure drop, i.e., a nominal pressure drop. The two way valves provide pressure relief in abnormal situations relative to nominal pressure for the check valve. In other words, operation, of the two-way aspect of the valve of the invention is in response to major pressure changes that deviate from the normal, expected operation of the duckbill valve, a one way check valve. Such major pressure changes arise from kinks in tubing or incorrect installation of the valve. When major pressure changes occur due to conduit kinks on either side of the valve, one of the positive and negative secondary flow paths is actuated to relieve the pressure difference. The secondary flow paths bypass the primary flow path until normal pressure is restored.

What is claimed is:

1. A two-way valve for cardio pulmonary bypass for operation at a nominal pressure drop, comprising:
    a tubular outer body supporting an axial duckbill valve operating as a check valve for fluid flow in a primary flow path at a first nominal pressure drop through the duckbill valve from a forward tubular member towards a rearward tubular member, the forward and rearward tubular members on opposite sides of the outer body;
    a pair of opposed valves each valve throttled by a nipple in the tubular outer body establishing positive and negative secondary flow paths activated at a second pressure drop through the duckbill valve, the secondary flow paths relieving the second pressure drop until the first nominal pressure drop is re-established.

2. The apparatus of claim 1 wherein the opposed valves are umbrella valves.

3. The apparatus of claim 1 wherein each secondary flow path is associated with an umbrella valve and a nipple arranged to throttle the umbrella valve.

4. The apparatus of claim 3 wherein each umbrella valve and nipple is separated by a flange with first and second holes, each hole between an umbrella valve and a nipple communicating pressure therebetween.

5. The apparatus of claim 4 wherein each umbrella valve has an apex, with one umbrella valve apex facing a hole and another umbrella valve apex facing away from a hole.

6. The apparatus of claim 4 wherein axially opposed forward and rearward tubular members are on opposite sides of the flange for establishing the primary flow path through the duckbill valve.

7. The apparatus of claim 1 wherein the umbrella valves are supported on a disk transverse to the axis of the duckbill valve.

8. The apparatus of claim 1 wherein the nipples face in the same axial direction.

9. The apparatus of claim 1 wherein the duckbill valve is made of silicone rubber.

10. The apparatus of claim 6 wherein the forward and rearward tubular members and the outer body are externally axially symmetric.

11. A two-way valve for cardio pulmonary bypass comprising:
    a tubular outer body having an axis and a radially annular flange extending inwardly within the body with first and second holes through the flange;
    a pair axially opposed forward and rearward tubular members each having an inner end seated in the tubular outer body on opposite sides of the annular flange and having fluid passageways facing the first and second holes;
    first and second umbrella valves disposed blocking the fluid passageways adjacent the rearward tubular member abutting the annular flange, the first umbrella valve having an apex facing the first hole and the second umbrella valve having an apex facing away from the second hole;
    a tubular duckbill one-way valve coaxially arranged in the tubular outer body and having first and second nipples with a central aperture covering the first and second holes adjacent the forward tubular member abutting the annular flange;
    wherein blockage of the rearward tubular member allows fluid flow around the second umbrella valve, through the second hole and the second nipple, while blockage of the forward tubular member allows fluid flow around the first umbrella valve, through the first hole and the first nipple and wherein the central apertures in said nipples throttle fluid flow allowing pressure imbalances on opposite sides of the duckbill valve to slowly equalize.

* * * * *